United States Patent [19]
Boerjan

[11] Patent Number: 6,149,956
[45] Date of Patent: Nov. 21, 2000

[54] METHOD FOR SELECTING EGGS

[75] Inventor: Maria Leonie Boerjan, Wageningen, Netherlands

[73] Assignee: Stichting Instituut Voor Dierhouderij en Diergezondheid, Netherlands

[21] Appl. No.: 09/110,598

[22] Filed: Jul. 6, 1998

[30] Foreign Application Priority Data

Jul. 7, 1997 [NL] Netherlands .......................... 1006504

[51] Int. Cl.$^7$ ...................................................... A23L 1/32
[52] U.S. Cl. ........................................... 426/231; 426/614
[58] Field of Search ................................... 426/231, 614; 356/56

[56] References Cited

FOREIGN PATENT DOCUMENTS 8 602 752   5/1988   Netherlands .

OTHER PUBLICATIONS

Database abstract, AN 96(09):Q0012. FSTA, Proceedings of Euro Fod Chem VIII, Vienna, Austria. vol. 1, pp. 143–149, 1995.

Database abstract, AN 78(06):A0340 FSTA, Dissertation Abstracts International, 37 (12), 1977.

F. Klammer et al, "Volume–Selective And Spectrosopically Resolved NMR Investigation Of Diffusion And Relaxation In Fertilised Hen Eggs", *Physics in Medicine and Biology* 35, Jan. 1990. No. 1, Bristol, GB, pp. 67–79.

U. Görke et al, "Detection of Anisotropic Pulsating flow and its Velocity–Fluctuation Rate in Fertilized Bird Eggs by NMR Microimaging", *Journal of Magnetic Resonance, Series B*, 111, pp. 236–242.

*Primary Examiner*—Anthony J. Weier
*Attorney, Agent, or Firm*—Michaelson & Wallace; Peter L. Michaelson; Edward M. Fink

[57] ABSTRACT

A method for selecting eggs, in which the eggs are subjected to a Nuclear Magnetic Resonance (NMR) treatment for obtaining an NMR image and the eggs are selected on the basis of the NMR image.

An apparatus for processing eggs includes egg supply means, egg selection means, and egg discharge means, the egg selection means having at least one apparatus for making at least one NMR image of an egg, and means being provided for controlling the egg discharge means on the basis of the at least one NMR image.

11 Claims, 1 Drawing Sheet

METHOD FOR SELECTING EGGS

This invention relates to a method for selecting eggs. A method according to the invention is characterized by the features according to claim 1.

For selecting eggs, for instance to determine whether an egg is fertilized or not, in known methods the egg is subjected to candling about seven days after laying. On the basis of the transparency to light, it is then determined whether the egg in question contains a living embryo. If this seems not to be the case, the egg is removed from the incubator in which it has been placed. A consequence of this known method is that a relatively large proportion of the eggs in an incubator will eventually not lead to a living chick. The space of the removed eggs will not be filled up again during the incubation process in question, yielding a relatively poor average occupation of the incubator during the incubation process. By way of illustration, in an incubation process for chicken eggs using an industrial incubator, about 20% of the eggs will not yield a living chick. About 10% of the eggs that are introduced into the incubator are found to be unfertilized. Moreover, this percentage increases as the age of the laying hens in question increases or when the health of the laying hens in question is not optimal. Also, the living conditions of the laying hens can adversely affect the ratio of fertilized to unfertilized eggs. A low average filling of an incubator is uneconomic.

Egg selection based on quantities other than embryo formation in the egg is not possible with the aid of the known candling procedure, at any rate is possible only to a very limited extent.

The object of the invention is to provide a method for selecting eggs, which obviates the above-mentioned disadvantages of the known method while maintaining the advantages thereof. To that end, a method according to the invention is characterized by the features according to claim 1.

The invention is based on the insight that in particular fertilization, but also, for instance, contamination by bacteria or a change in the ratio of egg white to egg yellow in an egg, lead to a specific change in, for instance, the proton configuration of at least a part of the egg, changes in the composition of the proteins in the egg and/or change in the cell structure of the egg, which changes are all observable in an early stage using a nuclear magnetic resonance technique and hence can be visualized using an NMR image. Also, differences can be determined which are the result of, for instance, the nutrition of the laying animal in question and genetic differences. These differences are in particular determinative of the quality of the egg.

NMR image should herein be understood to include at least Nuclear Magnetic Resonance (NMR) signals and combinations thereof, whether or not in processed or transformed form. Also understood to be encompassed are comparisons of, for instance, the amplitudes of one or more echo signals, relaxation times and/or relaxation velocities and the like, as well as other processing methods, conventional and known as such, for signals coming from NMR, for instance Magnetic Resonance Imaging (MRI).

The use of Nuclear Magnetic Resonance (NMR) for selecting eggs offers the advantage that in a particularly early stage after laying, a detailed image of the interior of an egg can be formed. The accurate NMR imaging, surprisingly, has been found to be particularly suitable for selecting the eggs according to different quantities. In doing so, use is made of differences in the resonance image of different kinds of eggs, which have arisen as a result of, for instance, fertilization, contamination by bacteria, differences in the ratio of egg white to egg yellow in the egg in question, and the like. Because substantially directly after the egg has been laid, a selection among the eggs can be effected using the NMR image, eggs are prevented from being incorrectly fed to a certain processing apparatus, which in turn prevents unnecessary egg spoilage during such a processing treatment. As a result, in each processing operation a relatively high efficiency is achieved.

In an advantageous embodiment, a method according to the invention is characterized by the features according to claim 2.

Surprisingly, it has been found that in particular, but not exclusively, fertilization of an egg leads to a specific change of the proton configuration, especially in the yolk of the egg in question, which is observable through an NMR treatment, even directly after laying. This means that especially determining this proton configuration, at least the change therein or deviations therefrom, is particularly suitable as a measure for the selection of the eggs. Because it has been found that such a change in the proton configuration occurs throughout the egg, and in particular throughout the yolk, consisting of yellow and white egg yolk, the advantage gained is that a high resolution and accuracy can be achieved relatively soon after laying.

In a first preferred embodiment, a method according to the invention is characterized by the features according to claim 3.

Using the NMR image, it can be established in a simple manner and relatively soon after laying, whether an egg is fertilized or not, whereupon the egg can be introduced into a suitable downstream path. The fertilized eggs, suitable for hatching, are then introduced into a first processing path, the other eggs into a second processing path, which eggs can be suitable, for instance, for consumption. This provides the advantage that all eggs that are supplied to the first processing path are fertilized and therefore, in principle, can lead to a living chick, with the degree of occupation of an incubator to be used to that effect being substantially optimal, while, in principle, all other eggs can be suitable for consumption. Unfertilized eggs are prevented from being supplied to an incubator, which would otherwise reduce the efficiency of the incubator while moreover eggs would be withdrawn from consumption. Accordingly, a double economic advantage can thus be achieved.

In further elaboration, a method according to the invention is characterized by the features according to claim 5.

Determining with the aid of an NMR image whether an egg contains a living embryo offers the advantage that those eggs that do not contain a living embryo can be taken from an incubator. This prevents the possibility of these last-mentioned eggs exploding in the incubator, which can lead to considerable fouling of the incubator. Moreover, exploding eggs can lead to contamination of the other eggs, and chicks issuing from them, with all its consequences.

In a second preferred embodiment, a method according to the invention is characterized by the features according to claim 6.

Contamination of an egg by bacteria leads to a change in the egg white and/or the egg yolk, for instance in the acidity, the composition of the proteins or the fat content. Such changes can be established easily and in an early stage with the aid of an NMR image, which enables selection of the eggs in an early stage. This means that in a simple manner bacterially contaminated eggs, or chicks issuing therefrom, can be prevented from being presented, for instance, for consumption or breeding. Contamination can thereby be prevented, so that safety is enhanced.

In a third preferred embodiment, a method according to the invention is characterized by the features according to claim 7.

Egg yellow and egg white exhibit different relaxation times, which can be visualized in an NMR image. Thus, the ratio between egg white and egg yellow in an egg can be determined in a simple manner. On the basis thereof, an egg can be supplied to a suitable processing path. It is noted in passing that also the nature of the egg yellow and/or the egg white can be determined in this way.

In a particularly advantageous embodiment, a method according to the invention is characterized by the features according to claim 8.

Comparing an NMR image of an egg with known NMR images provides the advantage of enabling automatic selection of the eggs on the basis of such a comparison in a particularly simple manner. Such a method can moreover be simply carried out with the aid of a self-learning apparatus, so that the accuracy and the rate of the egg processing can be maintained optimal at all times.

The invention further relates to an apparatus for processing eggs, which apparatus is characterized by the features according to claim 11.

With such an apparatus according to the invention, eggs supplied by the supply means can be subjected to an NMR treatment, whereupon the eggs can be readily selected on the basis of the NMR image obtained. Selection of the eggs then preferably consists in the eggs being introduced into a specific processing path by egg discharge means to be controlled on the basis of the NMR image.

In a particularly advantageous embodiment, a method according to the invention is characterized by the features according to claim 17.

Owing to the egg selection means being arranged for subjecting a series of eggs simultaneously to an NMR treatment, the egg processing rate of the apparatus can be considerably increased, in particular when a matrix of eggs can be subjected to an NMR treatment in one time. In particular the costs of making an NMR image are thereby reduced considerably, which is economically advantageous.

The invention further relates to the use of an NMR apparatus for selecting eggs, in particular fertilized eggs.

Further embodiments of a method or apparatus according to the invention are set forth inter alia in the subclaims.

For a better understanding of the invention, exemplary embodiments of a method and apparatus according to the invention will be explained with reference to the drawings. In the drawings.

Figure 1:
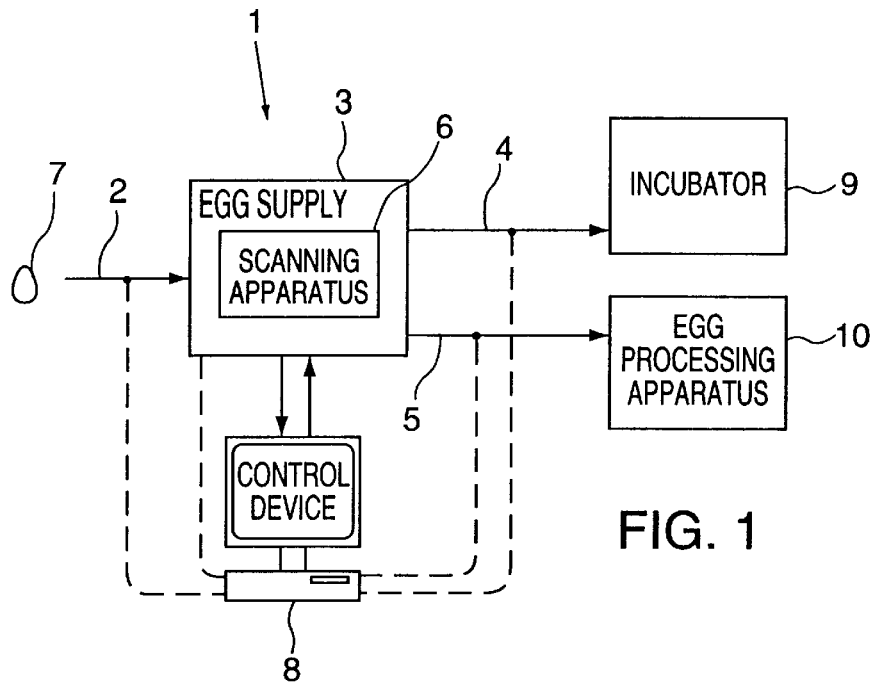
FIG. 1 shows a schematic representation of an egg selection apparatus according to the invention in a first embodiment.

An egg selection apparatus 1 according to FIG. 1 comprises egg supply means 2, egg selection means 3, first egg discharge means 4 and second egg discharge means 5. The egg selection means 3 comprise at least one scanning apparatus 6 for producing an image of an egg 7 being passed through the egg selection apparatus 1, using Nuclear Magnetic Resonance (NMR).

In the use of NMR technique, sensitive nuclei for this purpose, such as for instance hydrogen, are aligned parallel or at an angle to the axis of a magnetic field. Then use is made of radio frequency (RF) pulses for disturbing the alignment of some of these sensitive nuclei. Then use is made of the extent of release of energy by the nuclei upon removal of the RF pulses for obtaining an image of the structure from the nuclei in question. By making use of the distance of the different nuclei to the source of radiation and the receiver of the NMR apparatus, respectively, a clear image of each section of the object in question can be obtained, in which the structure is visible, distinguished according to the different types of nuclei, and hence of the physical structure of the object in question. When using NMR techniques, an object can be irradiated from one or more directions for obtaining different images. Using known techniques such as for instance Magnetic Resonance Imaging (MRI), from the radio frequency signals obtained, a clear (computer) image of each desired section can be obtained. For a further description of NMR and MRI techniques, reference is made to, for instance, "MRI for technologists" (1995), EDS Peggy Woodward/Roger Frimarck, McGrawhill Inc., or to "Magnetic Resonance in Medicine (1993): the basic text book of the European Magnetic Resonance form", Ed. P. A. Rinck, Blackwell Scientific Publishers, which publications are considered to be incorporated herein by reference.

Connected to the egg selection means 3 are the first and second egg discharge means 4, 5, which can be controlled by the egg selection means 3 on the basis of the NMR image obtained by the scanning apparatus 6. To that end, a control device 8, in the form of a computer, is connected to the egg selection apparatus 1. This control device 8 preferably comprises a data base storing a number of NMR images, of the same type as can be obtained with the scanning apparatus 6, of different types of eggs of known configuration. Further, this computer includes an algorithm for comparison of an NMR image coming from the scanning apparatus 6 with one or more relevant NMR images from the data base referred to. The algorithm is so designed that the extent of agreement between the NMR images referred to leads to a control signal for control of the egg discharge means 4, 5.

In the first embodiment shown, the first egg discharge means 4 connect to a hatching apparatus or incubator 9, the second egg discharge means 5 to an apparatus for e.g. making eggs suitable for consumption. In the incubator 9 a suitable number of eggs can be hatched under well-conditioned circumstances. Such incubators are generally known.

An egg selection apparatus 1 as shown in FIG. 1 can be used as follows.

Using egg supply means 2 suitable for the purpose, for instance a conveyor belt, an egg 7 is supplied to the first side of the egg selection means 3, where the egg 7 is routed through the scanning apparatus 6. The scanning apparatus 6 records at least one NMR image of the egg 7, which is transferred to the control device 8, where each recorded NMR image is compared with the relevant NMR images in the data base. For instance, the NMR image obtained using suitable RF pulses is compared with stored NMR images of (un)fertilized eggs of the same type. This comparison yields information on whether the egg in question is fertilized or not. Accordingly, on the basis of this comparison, it is determined if the egg is fertilized, whereupon the first egg discharge means 4 are controlled and the egg in question is supplied to the incubator 9. If the egg is not a fertilized egg, the second egg discharge means 5 are actuated and the egg 7 is discharged to the apparatus 10, for instance for processing for consumption. Through a suitable choice of the NMR technique, and the image to be thereby obtained, it is also possible, with the same or a similar egg selection apparatus, to sort out eggs on the basis of, for instance, contamination by bacteria, injuries or irregularities of the egg shell, the ratio between egg white and egg yolk, or the composition of, for instance, the egg yolk, to determine an optimum downstream route for each egg 7.

Figure 2:
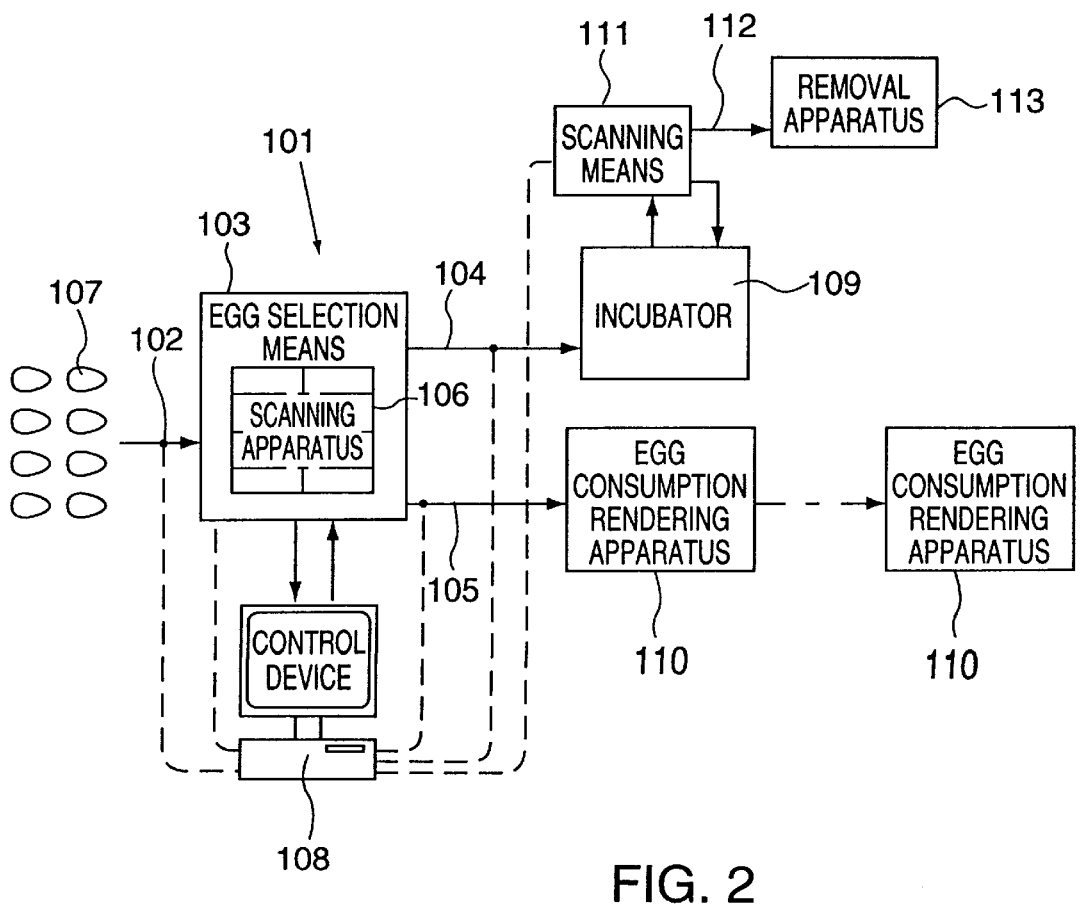
FIG. 2 shows an egg selection apparatus according to the invention in a second embodiment.

In the embodiment of an egg selection apparatus 101 as shown in FIG. 2, corresponding parts have corresponding reference numerals. In this egg selection apparatus 101, using suitable egg supply means 102, eggs 107 are supplied in an N×M matrix form. The eggs are supplied, for instance, row by row (N×1 matrix). In the egg selection means 103 a scanning apparatus 106 is included for simultaneously producing an NMR image of the N×M matrix of eggs 107. This image is again compared with relevant NMR images in the control device 108, whereupon the first and second egg discharge means 104, 105 can be controlled by the egg selection means 3 on the basis of the result of this comparison. The control device 8 is set such, and the first and second egg discharge means 104, 105 are arranged such, that for each individual egg 107 within the N×M matrix it can be determined whether it is to be discharged via the first 104 or the second egg discharge means 105. The second egg discharge means 105 are again connected to an apparatus 110, e.g. for making the eggs suitable for consumption. Such an apparatus 110 can consist, for instance, of a packaging apparatus, a processing apparatus, or the like. The first egg discharge means 104 again connect to an incubator 109.

Adjacent the incubator 109, second scanning means 111 are arranged for obtaining NMR images of one or more eggs 107 in the incubator 109. These second scanning means 111 are arranged for determining whether a living embryo is present in the or each egg 107 in question, in order to determine whether the egg in question should be maintained in the incubator or should be removed from it. These second scanning means 111 are likewise connected to the control device 108 for obtaining the desired control signal. On the basis of this control signal, third egg discharge means 112 can be actuated for transporting the eggs not containing a living embryo to a removal apparatus 113. This prevents the occurrence of exploding eggs in the incubator 109. 'Exploding eggs' should be understood to include at least eggs that explode in the incubator as a result of, for instance, gas accumulation in the egg. A disadvantage of such exploding eggs is that the incubator is thereby fouled considerably, while moreover there is a risk that the other eggs, and any subsequent issue, are infected and are thus rendered unsuitable for consumption or breeding.

Methods and apparatuses according to the invention are suitable in particular for processing chicken eggs, notably because of the large numbers of chicken eggs that are to be processed, but other eggs too can be selected with them. Thus, for instance eggs of other birds, but also eggs of reptiles, amphibians and fish can be selected according to different relevant quantities, such as fertilization, contamination and the like.

It has been found that, in any case upon fertilization of eggs, throughout the egg, in particular in the egg yolk, changes in the proton configuration occur, these changes being particularly well observable using NMR technique. This means that over a large surface a good resolution can be obtained, so that fertilization is more readily detectable. It is noted in passing that it is also possible to determine whether an egg is fertilized on the basis of the germinal disc in particular. The fact is that already by the time the egg is laid, which occurs approximately 24 hours after fertilization, such an extent of cell division will have occurred in the germinal disc that it is more simply detectable. For illustration, at lay, the fertilized germinal disc will consist of about 20,000 to 60,000 cells. This can be visualized by NMR, not by candling.

Use of MRI for the production of the NMR image provides the advantage that this is a known, conventionally used technique, yielding images that can be assessed both electronically and visually. This enables simple automation of an egg selection apparatus according to the invention, while visual inspection remains possible.

In the case of an egg selection apparatus according to the invention, processing apparatuses for the eggs, such as an incubator and a further processing apparatus, can be included directly downstream of the selection apparatus, but it is also possible to package the eggs after the selection and to transport them to other places for further processing. The selection then provides the advantage that no unnecessary transports of eggs occur, since each egg has been specifically selected for the specific processing apparatus.

As scanning apparatus for making an NMR image, a conventional NMR apparatus, known per se, can be used, and it may be specifically adapted for selecting eggs, in particular with regard to the magnetic field strength, the radio frequency pulses that are used, and the dimensions for passing through the specific eggs.

Presently, an example of a method according to the invention, carried out with a selection apparatus according to the invention, will be discussed.

EXAMPLE 1

Pilot experiment

NMR signals were recorded of unfertilized and fertilized eggs in an NMR apparatus with a probe diameter of 4.5 cm, and a magnetic field of 0.5 Tesla (22.3 MHz). The eggs were centered in the NMR probe using a cardboard trough. The trough had a circular hole (app. 2 cm, diameter) in which fitted the egg at its largest diameter, such that the round hole coincided with the center of the probe. In this simple manner, new eggs were successively located in the center of the probe. Then NMR signals were recorded of a 'slice', a section in the longitudinal direction of the egg (or perpendicular thereto) through the center of the egg and hence through the yellow and white (the so-called latebra on which lies the germinal disc in the center of the yolk). For the recording, an RT (repetition time) of 1500 ms and a TEI of 45 ms were used. Then various computer calculations were performed on the signals. It was found that very clear differences are observable in the MRI images of fertilized and unfertilized eggs as a result of differences in T1 and T2 relaxation times. These differences were visualized using an MRI image. It is noted in passing that the differences can also be visualized, for instance, after Fourier transformation in the amplitude of one of the echoes or in another way.

By way of illustration, a number of data regarding chicken eggs in the Netherlands are given, which are not to be construed as limiting in any manner.

In the Netherlands, annually (1997) about 800 million chicken eggs are produced as hatching eggs. By carrying out an egg selection according to the invention as described above prior to placing the eggs in an incubator, the hatching process can be started with fewer eggs, yielding the same number of chicks. Research has demonstrated that a proper selection can lead to a reduction of about 10% of the required eggs to obtain the same number of chicks. A large part of the unfertilized eggs removed during the selection can be subsequently used for consumption. This means that the economic advantage is achieved by, on the one hand, a better occupation of the incubators and, on the other, an increased supply of consumption eggs.

The invention is not in any way limited to the exemplary embodiments set forth in the description and drawings. Many variations thereof are possible.

Thus, each egg selection apparatus can comprise a different number of scanning devices for obtaining multiple NMR images of each egg or a number of NMR images of different eggs simultaneously. With the different scanning devices, different images can be obtained for, for instance, successively obtaining insight into the fertilization of an egg in question, any contamination thereof and/or the egg white/egg yellow ratio, while the making of each next NMR image can be made dependent on the result of the preceding NMR image. Further, the egg selection means and the control device can be arranged for controlling more than two egg discharge apparatuses, for instance to make a distinction between the eggs according to several classes of egg white to egg yellow ratio, egg size, egg yellow and/or egg white composition and the like. Also, an egg selection apparatus according to the invention can include other means for determining selection criteria for the eggs, such as conventional egg candling, weighing means, means for recording the shape and size of the egg in question and the like, which means, together with the egg selection means as described hereinabove, can be used for selecting the eggs.

These and many similar embodiments are understood to fall within the scope of the invention.

What is claimed is:

1. A method for selecting eggs based upon the fertilized and unfertilized status thereof wherein the eggs are subjected to a Nuclear Magnetic Resonance (NMR) treatment for obtaining an NMR image, and the eggs are selected on the basis of the differences between the NMR images of fertilized and unfertilized eggs.

2. A method in accordance with claim 1 wherein with the aid of the NMR image a proton configuration in at least a part of the eggs is determined.

3. A method in accordance with claim 1 wherein it is determined whether the eggs subjected to NMR treatment are fertilized, whereupon fertilized eggs are directed to a first processing path and unfertilized eggs to a second processing path.

4. A method in accordance with claim 1 wherein with the aid of the NMR image it is determined whether cell division in the germinal disc of the egg has occurred as a result of fertilization.

5. A method in accordance with claim 1 wherein with the aid of the NMR image it is determined whether in the eggs subjected to NMR treatment a living embryo is present, whereupon eggs without a living embryo are separated from eggs with a living embryo.

6. A method in accordance with claim 1 wherein with the aid of the NMR image it is determined whether the egg in question is contaminated by bacteria.

7. A method in accordance with claim 1 wherein with the aid of the NMR image the egg yellow to egg white ratio in the eggs is determined, and on the basis of this determination further processing for the eggs is determined.

8. A method in accordance with claim 1 wherein the NMR image of an egg is compared with NMR images stored in a data base, and further processing for the egg is determined on the basis of the result of this comparison.

9. A method in accordance with claim 1 wherein Magnetic Resonance Imaging (MRI) is used for the NMR image.

10. A method in accordance with claim 1, wherein with the aid of one or more NMR images, a change in or a shift of a resonance spectrum of an egg is determined.

11. Use of an NMR apparatus for selection of fertilized and unfertilized eggs based upon the differences between the NMR images of fertilized and unfertilized eggs.

* * * * *